United States Patent [19]

Fiato et al.

[11] Patent Number: 4,532,229
[45] Date of Patent: Jul. 30, 1985

[54] PROCESS FOR PREPARING A FE-CO CATALYST SLURRY SYSTEM FOR ALPHA OLEFIN PRODUCTION

[75] Inventors: Rocco A. Fiato, Scotch Plains; Gary B. McVicker, Califon; Angelo A. Montagna, Summit, all of N.J.

[73] Assignee: Exxon Research and Engineering Co., Florham Park, N.J.

[21] Appl. No.: 561,221

[22] Filed: Dec. 14, 1983

[51] Int. Cl.$^3$ .................. B01J 21/04; B01J 23/78
[52] U.S. Cl. ................ 502/330; 502/260; 502/304; 502/328; 502/336; 502/338
[58] Field of Search ............. 502/260, 304, 328, 330, 502/336, 338

[56] References Cited

U.S. PATENT DOCUMENTS

| | | | |
|---|---|---|---|
| 2,662,090 | 12/1953 | Scharmann | 260/449.6 |
| 2,686,195 | 8/1954 | McAdams et al. | 260/449.6 |
| 2,735,862 | 2/1956 | Buchmann et al. | 260/449.6 |
| 2,850,515 | 9/1958 | Riblett | 260/449.6 |
| 4,154,751 | 5/1979 | McVicker et al. | 260/449.6 R |

FOREIGN PATENT DOCUMENTS 2050859A 1/1981 United Kingdom .

OTHER PUBLICATIONS

"The Synthesis of Light Hydrocarbons from CO and H$_2$ Mixtures over Selected Metal Catalysts", by M. K. Zaman Khan et al., ACS 173rd Symposium, Fuel Division, New Orleans, Mar. 1977.
"Mossbauer Spectroscopy of Supported Fe-Co Alloy Catalysts for Fischer-Tropsch Synthesis"—Journal of Catalysts, vol. 72, pp. 37-50, (1981).
"Mossbauer and Magnetic Studies of Bifunctional Medium-Pore Zeolite-Iron Catalysts Used in Synthesis Gas Conversion"—Advances in Chemistry Series, 1981, pp. 573-588, by Lo et al.
"Mossbauer Effect in Iron and Dilute Iron Based Alloys"—Physics Reports (Section C of Physics Letters) 12, No. 5, (1974), pp. 335-374.
Gmelins Handbuch der Anorganische Chemie, vol. 8, Auflage, (1959), pp. 408-413 and 1160-1161.
Hydrocarbon Processing, May 1983, pp. 88-96.
Chem-Ing.-Tech. 49, (1977), (Nos. 6: pp. 463-468, (1977), by D. Kitzelmann et al., German.
C.R. Acad. Sc. Paris, p. 268, (May 28, 1969), by P. Courty and B. Delmon.
"Fischer-Tropsch Synthesis with Iron-Cobalt Alloy Catalysts"—Stud. Surf. Sci. Catal. 7, Part A, pp. 432-446, (1981), (English).
AIChE 1981 Summer National Meeting, Detroit, Preprint No. 408, (English).
Journal of Materials Science 7, (1972), pp. 1383-1390, by A. C. C. Tseung, and J. R. Goldstein.
ACS Meeting, Division of Petroleum Chemistry, Mar. 1978, entitled "Catalytic Synthesis of Light Olefinic Hydrocarbons from CO and Hydrogen Over Some Iron Catalysts", by C. H. Yang and A. G. Oblad.
Journal of Catalysis 32, pp. 452-465, (1974), by J. R. Goldstein et al.
J. Phys. Chem. Solids, 1959, vol. 9, pp. 165-175, by G. H. Jonker.
"The Fischer-Tropsch and Related Synthesis", by Storch, Golombic and Anderson, (Wiley), pp. 242-243.
Catal. Rev.-Syn. Eng. 21 (2), pp. 225-274, (1980).
J. Phys. Chem. Solids, 1976, vol. 37, pp. 619-624, by P. J. Murray and J. W. Linnett.
"Numerical Data and Functional Relationships in Science and Technology", Landolt-Bornstein, New Series, vol. 12, part B, Magnetic and Other Properties of Oxides and Related Compounds:Spinels, Iron Oxides and Iron-Metal-Oxygen Compounds, editor K. H. Hellwege, pp. 245-250.
Kirk-Othmer, "Encyclopedia of Chemical Technology", 3rd Edition, vol. 13, pp. 90-95.
Journal of Catalysis, vol. 72, pp. 95-110, (1981), by J. A. Amelse, L. A. Schwartz and J. B. Butt.
Hydrocarbon Processing, Nov. 1980, pp. 139-142, "Make Olefins from Syn Gas", by V. U. S. Rao and R. J. Gormley.
Z. Physik Chemie Neue Folge 112, 215-233, (1978), by Kitzelman et al., "In Situ Study of the Primary Reactions in the Hydrogenation of CO on Iron Catalysts".
J.C.S. Chem. Comm., pp. 428-430, (1983).

*Primary Examiner*—W. J. Shine
*Attorney, Agent, or Firm*—R. J. North; Edward M. Corcoran

[57] ABSTRACT

The use of relatively stable iron carbonyl complexes e.g. Bis(dicarbonylcyclopentadienyliron), and lower melting cobalt carbonyl complexes, facilitates production of mixed metal catalysts for conversion of CO/H$_2$ to alpha-olefins. The decomposition of these materials can be achieved in a controlled manner resulting in an excellent alpha-olefins synthesis catalyst in Fischer-Tropsch processes.

18 Claims, No Drawings

PROCESS FOR PREPARING A FE-CO CATALYST SLURRY SYSTEM FOR ALPHA OLEFIN PRODUCTION

BACKGROUND OF THE INVENTION

1. Field of the Invention

This invention relates to a process for producing alpha olefins in a Fischer-Tropsch synthesis utilizing slurried Fe-Co catalyst system derived from the in situ decomposition of Fe and Co metal carbonyl complexes.

2. Brief Description of the Prior Art

Fischer-Tropsch processes using iron-based catalysts including cobalt as a co-catalyst, are known to produce gaseous and liquid hydrocarbons containing $C_2$–$C_4$ olefins. Because of the importance of $C_2$–$C_4$ olefins, particularly as feedstocks for the chemical industry, modifications of the Fischer-Tropsch process are constantly being pursued toward the goals of maximizing $C_2$–$C_4$ olefin selectivity while maintaining high catalyst activity and stability under the reaction conditions. The main thrust of the efforts in this area has been in the area of new catalyst development.

Disclosures in the art directed to Fischer-Tropsch processes employing iron-cobalt catalysts and alloys and/or description of these general types of catalyst materials, include: U.S. Pat. No. 2,850,515; U.S. Pat. No. 2,686,195; U.S. Pat. No. 2,662,090; U.S. Pat. No. 2,735,862; AICHE 1981 Summer Nat'l Meeting Preprint No. 408, "The Synthesis of Light Hydrocarbons from CO and $H_2$ Mixtures over Selected Metal Catalysts", ACS 173rd Symposium, Fuel Division, New Orleans, March 1977; J. Catalysis 1981, No. 72(1), pp. 37–50; Adv. Chem. Sec. 1981, 194, 573–88; Physics Reports (Section C of Physics Letters) 12 No. 5 (1974) pp. 335,374; UK Patent Application No. 2050859A; J. Catalysis 72, 95–110 (1981); Gmelins Handbuch der Anorganische Chemie 8, Auflage (1959), pp. 59; Hydrocarbon Process, pp. 81–96 (May 1983); Chem-Ing.-Tech. 49 (1977) Nr. 6, pp. 463–468; and U.S. Pat. No. 4,154,751.

In this technology, it is also known that high levels of cobalt in an iron-cobalt alloy can produce enhanced selectivity to paraffinic products, as described in *Stud. Surf. Sci. Catal.* 7, Pt A, pp. 432 (1981).

The reference *J.C.S. Chem. Comm.* p. 428–430 (1983) describes complexes such as $HFeCo_3(CO)_{12}$ which can effectively be supported on basic supports such as silica modified by amino donor functions. The complexes are described as yielding active FischerTropsch catalysts giving rise to an unusual hydrocarbon product distribution.

A recent trend in the development of Fisher-Tropsch synthesis of alpha olefins has been in the area of slurry catalysis as opposed to fixed bed catalysts synthesis. An advantage of the slurry process is that better control of heat dissipation and catalyst maintenance can be achieved. Particularly what is being sought is a technique for preparing the slurry catalyst, which must be finely divided for good catalyst activity, in situ in the slurry liquid, as opposed to the ex situ preparation which is generally practiced in the art as described in the above reference.

SUMMARY OF THE INVENTION

It has been found that slurried Fe-Co catalysts for the conversion of $CO/H_2$ to alpha-olefins can be prepared by the in situ decomposition of individual, readily available, Fe and Co carbonyl complexes directly in the slurry liquid wherein the Fe complex has a higher melting point/decomposition temperature than the corresponding Co complex being employed. The difference in melting point/decomposition temperature facilitates sequential deposition of Co and Fe onto the support nucleation sites and allows greater control over the surface composition and particle size of the resulting mixed metal catalyst than that achieved with conventional methods, such as described in U.S. Pat. No. 4,154,751, which discloses the use of metal carbonyl precursors for production of fixed-bed catalysts. Catalysts employed in U.S. Pat. No. 4,154,751 are prepared ex situ with unusual precautions required to exclude $O_2$ containing gases and to passify the catalyst before transfer to the reactor. In contrast, catalysts of the present process can be readily prepared in situ, precluding the need for the anaerobic procedures and transfer steps which are part of previously disclosed procedures.

The process is generally carried out by placing the iron and cobalt carbonyl complex materials in a liquid hydrocarbon used as a slurry liquid, e.g. octacosane or hexadecane, and charged to a stirred tank slurry reactor. The system is purged with an inert gas such as nitrogen, and then charged with carbon monoxide at from 50 to 100 pounds per square in. gauge (psig) pressure before being heated to 150°–250° C., usually about 200° C. A hydrogen rich gas, e.g., 9:1 mole ratio of $H:N_2$ is then fed to the system at a feed rate of about 800 to 1000 standard volumes of gas per volume of original catalyst charged per hour. The system is maintained under these conditions for a period of about 1 to 3 hours during which time the carbonyl complexes undergo decomposition to form the active catalyst.

The iron to cobalt atomic ratio of the slurry catalyst mixture can be controlled by varying the proportions of the carbonyl complexes initially charged to the system. The iron to cobalt atomic ratio present in the charged carbonyl complexes useful in the process is generally from about 1:1 to about 10:1, preferably from about 2:1.

A preferred subject Fe-Co catalyst for the production of alpha-olefins can be prepared by the in situ liquid slurry decomposition of a mixture of $Co_2CO_8$ and $[Cp\ Fe(CO)_2]_2$, wherein the iron complex has a higher melting/decomposition temperature than the cobalt complex, 194° C. dec. vs 51°–52' C. dec. The symbol "Cp" represents the cyclopentadienyl ligand, $C_5H_5$.

In accordance with this invention there is provided a process for preparing a slurried Fischer-Tropsch catalyst system comprising the steps of:

(a) heating a slurry mixture comprised of: a Fischer-Tropsch slurry liquid, an iron carbonyl compound, a cobalt carbonyl compound, or iron and cobalt compounds capable of forming carbonyl complexes in a CO atmosphere, or mixtures thereof, and a powdered support; wherein the cobalt carbonyl compound has a lower melting point/decomposition temperature than the iron carbonyl compound; in a carbon monoxide atmosphere under pressure, at a temperature above the melting point/decomposition temperature of the cobalt compound for a time sufficient to substantially decopose the carbonyl compound; and (b) heating said slurry mixture from step (a) at a temperature above the melting point/decomposition temperature of the iron compound in said carbon monoxide atmosphere under pressure, to substantially decompose the iron compound; and (c) heating said slurry mixture from step (b) in an atmosphere of hydrogen gas to substantially reduce said iron and cobalt carbonyl compounds and their decomposition products.

Further provided is a Fischer-Tropsch liquid slurry catalyst system comprising the decomposition and reduction products of a mixture of iron and cobalt compounds in a slurried liquid obtained by the above-described preparative process.

In addition there is provided a process for synthesizing a hydrocarbon mixture containing $C_2$–$C_4$ alpha olefins comprising the step of contacting a liquid slurry catalyst system produced by the process described above, with a mixture of CO/hydrogen under reaction conditions of pressure, space velocity and elevated temperature for a time sufficient to produce said $C_2$–$C_4$ olefins.

DESCRIPTION OF THE INVENTION AND PREFERRED EMBODIMENTS

The subject process for producing the slurry Fischer-Tropsch catalyst process described hereinabove is comprised of three steps.

The first step comprises heating a liquid slurry mixture containing a Fischer-Tropsch slurry liquid, an iron carbonyl compound, a cobalt carbonyl compound, and a powdered support and optionally a promoter agent. The iron and cobalt carbonyl compounds maybe preformed, i.e., [CpCo(CO)$_2$], [CpFe(CO)$_2$] or may be formed in situ in the liquid slurry mixture under an atmosphere of CO by using precursors such as (Cp)$_2$Fe and (Cp)$_2$Co. The carbonyl iron and cobalt compounds can be preformed or formed in situ, can be soluble or partially soluble in the slurry liquid used, and are preferably soluble.

The characteristic aspect of the first step is that the cobalt carbonyl compound has a lower melting point/decomposition temperature than the iron carbonyl compound. It has been found by us that the use of the lower melting cobalt compound allows the dispersion of the cobalt compounds onto nucleation sites first. This then allows for a more active and reproducible catalyst as opposed to that of a lower or similar temperature iron-containing carbonyl catalyst. Other characteristics of the use of the lower melting cobalt carbonyl compound will give rise to a catalyst which initially will contain a higher level of iron on the surface.

The in situ decomposition of the cobalt carbonyl compound in the first step is conducted by the heating of the slurry mixture at the appropriate temperature above that of the cobalt carbonyl compound and below that of the iron compound decomposition temperature. Generally the temperature is in the range of about 60° to 250° C., and preferably of about 100° to 200° C.

The heating is conducted under an atmosphere of CO, at a CO partial pressure of about 15 to 200 psia, and preferably 50 to 100 psia. The function of the carbon monoxide atmosphere is to insure the stability of the carbon monoxide compounds as they deposit onto nucleation sites which are on the support used. Other functions of the carbon monoxide atmosphere are to moderate the rate of decomposition of the carbonyl compounds in the reactor.

The second step of the process involves heating the slurry mixture which contains the cobalt carbonyl compound which has been decomposed, at a temperature to decompose the iron carbonyl compound. Generally this temperature ranges from 100° to 300° C. and preferably 180° to 250° C. The decomposition of the iron cobalt compound is also conducted under the CO atmosphere to stabilize the formed carbonyl decomposition products on the nucleation sites in the slurry liquid. Generally the CO partial pressure is the same as used in the first step and is in the range of about 15 to 200 psia and preferably 50 to 100 psia. The heating step is conducted for a time sufficient to substantially decompose the iron carbonyl compound in the second step.

The third step in the process involves the heating of the slurry mixture containing the decomposed iron and cobalt carbonyl compounds at an elevated temperature in a hydrogen atmosphere for a time and period sufficient to substantially reduce said decomposed iron and cobalt carbonyl compounds and their decomposition products. The temperature is generally in the range of about 100° to 300° C., preferably 180° to 280° C. for the step and the hydrogen partial pressure is generally 15 to 200 psia and preferably 50 to 100 psia.

Slight modifications can be made with the proviso that the liquid slurry mixture is heated under a CO atmosphere such that the cobalt carbonyl compound is substantially decomposed first in the process then followed by the decomposition of the iron carbonyl compound at a higher temperature, followed by heating the resulting mixture in an atmosphere of hydrogen to substantially reduce the iron and cobalt forms resulting from their decomposition. Alternatively, the cobalt compound can alone be added and decomposed followed by addition of the iron carbonyl to the reaction mixture with subsequent decomposition to generate the active catalyst.

The iron carbonyl compounds and carbonyl compound precursors which are useful in the process have the following characteristic a decomposition-melting point in the range of 100° to 200° C. Representative examples include: [CpFe(CO)$_2$]$_2$, (Cp)$_2$Fe, Fe$_3$(CO)$_{12}$, CpFe(CO)$_2$I, and related alkyl substituted cyclopentadienyl analogs including those where Cp (cyclopentadienyl ligand) can additionally be substituted with preferably 1 to 5 $C_1$–$C_4$ linear or branched alkyl groups, i.e. methyl-cyclopentadienyl, 1,3-diethylcyclopentadienyl, 1,2,3,4,5-pentamethylcyclopentadienyl, and the like. Other substituents for the cyclopentadienyl ring may also be used providing they are inert or unreactive under the process conditions herein. A preferred iron carbonyl compound in the process is [CpFe(CO)$_2$]$_2$, bis(dicarbonylcyclopentadienyliron).

The cobalt carbonyl compounds and carbonyl compound precursors which can be used in the process must have a lower melting point/decomposition temperature than the corresponding iron carbonyl compounds. The decomposition temperature should fall in the range of 25° to 180° C. Representative examples of cobalt compounds useful in the process include: Co$_2$(CO)$_8$, CpCo(CO)$_2$, (Cp)$_2$Co, and related alkyl substituted cyclopentadienyl analogs, as defined and described for the respective iron compounds. A preferred cobalt carbonyl compound useful in the process is Co$_2$(CO)$_8$.

The amount of iron and cobalt carbonyl compounds are chosen such that the iron:cobalt atomic ratio of the materials in the mixture is in the region of about 35:1 to 1:10 taken as the free metals, in the overall liquid slurry mixture, which ratio is the same at the start and finish of the process. Preferred is where the iron to cobalt atomic ratio used in the slurry is in the range of about 35:1 to 1:7, the most preferred ratio is 19:1 to 0.5:1.

A metal oxide support phase is also preferred in the process as it appears to minimize metal plating on the slurry reactor walls during iron and cobalt carbonyl decomposition and reduction steps. The specific support phase used may also influence catalyst performance by affecting the morphology of the iron and cobalt crystallites or by altering the overall chemisorption properties of the catalyst. Representative metal oxides which are useful as supports include Group II to VII oxides and rate earth oxides including alumina, magnesia, $Fe_2O_3$, $SiO_2$, $CeO_2$, mixtures thereof, and the like. Preferred supports for the present catalysts are $Fe_2O_3$ and magnesia. A requirement for the support in the slurry system is that it be thermally stable under the conditions of CO/hydrogen hydrocarbon synthesis in the slurry liquid mixture. The support if used is utilized in a 10 to 99 weight percent based on the total amount of iron and cobalt compounds and support used in the process. A preferred range of utilizing the support is in a 80 to 99 weight percent of the total weight of iron and cobalt compounds and support which are used. Preferably, the support has a promoter agent deposited thereon.

A promoter agent can also be used in the composition and can be used to particularly promote olefin formation in the process. Representative examples of classes of suitable promoter agents include carbonates, bicarbonates, organic acid and inorganic acid salts, e.g. acetates, nitrates, halides, sulfates, and hydroxide salts of Group IA and IIA metals including lithium, sodium, potassium, rubidium, cesium, barium, strontium, magnesium, copper and the like. These promoters may also be added to the system as individual components, for example potassium methoxide or as components of the starting carbonyl complex, eg., $KCo(CO)_4$, potassium tetracarbonyl cobaltate, to be deposited on the metal oxide support during the catalyst pretreatment step.

Representative examples of specific promoter agents are: potassium carbonate, potassium sulfate, potassium hydroxide, potassium chloride, cesium chloride and the like. A particularly preferred promote agent is potassium carbonate. The promoter is used is generally present in about a 0.1 to 10 weight percent of the total combined amount of iron and cobalt compounds and support used. A preferred level of promoter agent is in the range of one to two weight percent of the total combined weight of iron and cobalt carbonyl compounds and support used. A preferred support/promoter agent combination is $Fe_2O_3$/1 wt.% $K_2CO_3$.

The slurry liquid used is chemically inert under the reaction conditions and should be a relatively good solvent for CO/hydrogenation and possess good slurrying and dispersing properties for the finely divided catalyst. Other properties of the slurry liquid medium include a boiling point $> 100°-300°$ C., and high thermal stability at temperatures of $200°-300°$ C. Representative classes of slurry liquid useful are: high boiling aliphatic and aromatic hydrocarbons, ethers, amines, and mixtures thereof. The high boiling paraffins include $C_{10}-C_{50}$ linear or branched paraffinic hydrocarbons; the aromatic hydrocarbons include $C_7-C_{20}$ single ring and multi-and fused ring aromatic hydrocarbons; the ethers include aromatic ethers and substituted aromatic ethers where the ether oxygen is sterically hindered from being hydrogenated; the amines include long chain amines which can be primary, secondary, and tertiary amines wherein primary amines preferably contain at least one $C_{12}$ alkyl group in length, secondary amines preferably contain at least two alkyl groups being $C_7$ or greater in length, and tertiary amines preferably contain at least three alkyl groups being $C_6$ or higher in length. The slurry liquid can contain N and O in the molecular structure but not S, P, As or Sb, since these are poisons in the slurry process. Representative examples of specific slurry solvents are dodecane, hexadecane, octadecane, cosane, tetradecane, tetracosane, octacosane, triocontane, dotriacontane, hexatriacosane, tetratetracontane, toluene, tetracontane, o-, m-, and p-xylene, mesitylene, $C_1-C_{12}$ mono- and multi-alkyl substituted benzenes, dodecylbenzene, naphthalene, anthracene, biphenyl, diphenylether, dodecylamine, diheptylamine, trioctylamine, and the like. Preferred slurry liquids are octacosane, hexadecane, or mixtures thereof.

The amount of slurry liquid present is in a 50:1 to 99:1 weight ratio to the total amount of iron and cobalt compounds and support and promoter agent present. Preferably an 80:1 to 95:1 weight ratio of slurry liquid to total weight of Fe and Co compounds, support and promoter agent, is used.

One preferred embodiment is where the liquid slurry mixture contains cobalt carbonyl, $Co_2(CO)_8$, plus iron carbonyl compound $(CpFe(CO))_2$ plus iron oxide support $(Fe_2O_3)$, having one weight percent potassium carbonate deposited thereon, wherein the weight ratio of the cobalt compound:iron compound:iron oxide support is about 0.94:0.304:1.0, and the slurry liquid is octacosane which mixture is heated at a temperature of about 200° C. in a carbon monoxide atmosphere of about 100 psig partial pressure to substantially decompose the cobalt and iron carbonyls, then heating the resulting mixture at 220° C. in a hydrogen atmosphere at 100 psig to substantially reduce any formed iron or cobalt carbonyl compounds or their decomposition products remaining in the mixture. The slurry catalyst is then useful in a Fischer-Tropsch slurry mixture for producing hydrocarbons containing significant amounts of olefins.

Also a subject of this invention is the liquid slurry mixture containing the decomposed and reduced iron and cobalt carbonyl compounds in the presence of a support and promoter agent as described hereinabove.

Also a subject of the instant invention is a Fisher-Tropsch slurry process for producing $C_2-C_4$ alpha olefins by utilizing the iron-cobalt liquid slurry catalyst medium described hereinabove, wherein the CO/hydrogen mixture is forced through the catalyst slurry allowing good contact betwween the CO/hydrogen and the suspended catalyst to initiate and maintain the hydrocarbon synthesis process.

Advantages of a slurry process over that of a fixed bed process are that there is better control of the exothermic heat produced in the Fishcher-Tropsch process during the reaction and that better control over replenishing an upgrading catalyst for catalyst maintenance purposes. The slurry process can be operated in a batch or in a continuous cycle, wherein the continuous cycle, the entire slurry is circulated in the system allowing for better control of the catalyst-gaseous reactant mixing.

The amount of catalyst used in the slurry liquid is described hereinabove.

The catalyst slurry system, comprised of the slurry liquid and finally divided catalyst, prepared from the iron and cobalt carbonyl precursors, support and promoter agent, is generally stirred to promote good dispersion in the process and to avoid catalyst settling. in a laboratory continuous stirred tank Parr ™ reactor unit the rate of stirring is generally carried out in the range of about 500 to 2000 rpm and preferably 600 to 1200 rpm. Higher or lower values may also be used successfully, but in general, high values tend to lead to more efficient transport of reactant gas to the catalyst surface, and lower values tend to lead to a diffusion limited operating modes wherein reaction rate and the formation of high molecular weight products is limited.

Prior to the CO/hydrogen hydrocarbon synthesis run, the reduced and carbided iron cobalt catalyst is generally conditioned in the apparatus by purging with nitrogen to remove reactive gases and then the temperature is increased while stirring to the reaction temperature range. Then the system is generally subjected to a hydrogen treatment for a sufficient time to insure complete removal of any surface Group VIII metal oxide which interferes in hydrocarbon synthesis. The pressure and space velocity during the conditioning step are not critical and can be utilized in the range which is actually used during actual hydrocarbon synthesis.

Following the conditioning step, the CO/hydrogen feedstream is introduced into the catalyst chamber and the pressure, space velocity, temperature, and hydrogen: CO molar ratio is then adjusted as desired, for hydrocarbon synthesis conditions.

In the process, the hydrogen and CO are used in a hydrogen/CO molar ratio in the gaseous feedstream of about 0.5:1 to 7:1 molar ratio and preferably 0.6:1 to 2:1. Higher molar ratios tend to lead to a more paraffinic product and lower molar ratios tend to lead to excessive formation of carbon deposits on the catalyst surface and net loss of activity.

The temperature in the process is generally in the region of about 200° to 300° C. and preferably being 230° to 280° C. Higher temperature ranges can also be used but tend to lead to a more paraffinic $C_1$–$C_4$ selectivity, lower temperature ranges can also be used but tend to lead to reduced activity.

The pressure useful in the process is generally conducted in the range of about 15 to 450 psig and preferably about 60 to 300 psig. Higher pressures can also be used but tend to lead to higher levels of wax, and lower pressures can also be successfully used but tend to lead to higher levels of methane and lower rates.

The space velocity, expressed as standard hourly space velocity, SHSV, used in the process is generally about 400 to 2000 volume of gaseous feedstream/per volume of dry catalyst per hour and is preferably in the range of about 800 to 1200 V/V/hr. Higher space velocities can also be used but tend to lead to more difficult product/reactant separation schemes, and lower space velocities can also be used but tend to lead to lower selectivity to alpha-olefins.

By the use of the above-described catalyst slurry system, the activity maintenance is very good and on a laboratory scale, e.g. 50 cc of slurry containing 5–10 g of an Fe/Co/Fe$_2$O$_3$/1%K supported, catalyst, 5–10 days of continuous run have been observed without significant decline in percent CO conversion activity while maintaining good $C_2$–$C_4$ olefin synthesis activity.

The percent CO conversion obtainable in the subject process while providing substantial quantities of $C_2$–$C_4$ olefins, ranges from about 20 to 80 percent and preferably about 30 to 60 percent for sufficient $C_2$–$C_4$ olefin production. Higher and lower percentages of CO conversion may be utilized but very high percent CO conversions lead to more paraffinic products, while low percent CO conversions lead to difficulties in separating products from reactant gas.

"Total hydrocarbons" produced in the process, with selectivity related to the percent CO conversion to hydrocarbons, the hydrocarbons being from $C_1$ to about $C_{40}$ inclusive, is generally 0 to 50 percent of the total CO converted, the rest being converted to $CO_2$.

The percent $C_2$–$C_4$ hydrocarbons of the total hydrocarbons produced including $C_1$–$C_{20}$ and above is about 10 to 60 wt.% and usually about 15 to 50 wt.%. The percent of $C_2$–$C_4$ olefins produced of the $C_2$–$C_4$ total hydrocarbons produced is about 50 to 95 wt.% and usually about 70 to 90 wt.% of the $C_2$–$C_4$ total hydrocarbons.

As a percent of the total hydrocarbons produced, the percent $C_2$–$C_4$ olefins produced is about 20 to 60 wt.% and usually about 15 to 35 wt.%.

The present selectivity to methane based on the amount of CO conversion is about 2 to 10 percent. Preferably about 3–8 percent and lower methane is produced in the process.

The $C_5+$ hydrocarbon fraction in the process is generally produced in about 20 to 70 percent and usually about 30 to 50 percent. Higher amounts of $C_5+$ hydrocarbons can be obtained in the process by operating at higher pressures and lower temperatures.

As discussed above the percent selectivity to $CO_2$ formation in the process is about 10 to 60 percent.

Preferably the reaction process variables are adjusted to minimize $CO_2$ production, minimize methane production, maximize percent CO conversion, and maximizing percent $C_2$–$C_4$ olefin selectivity, while achieving activity maintenance in the catalyst system.

Generally, this format can be derived in a preferred mode of operating the process where the liquid hydrocarbon used is octacosane, the catalyst used is Fe/Co/Fe$_2$O$_3$/1%K, see Table I through D below, the catalyst/liquid hydrocarbon weight ratio is 1:9, the system is stirred at 600–1200 rpm, and pretreatment procedure of heating to 200° C. over 3–4 hr at 100 psia followed by $H_2$ at 220° C. for 1 hr and then exposing the catalyst to CO hydrogenation conditions, the CO/hydrogen molar ratio is 1:1, the temperature is maintained in the range 250°–280° C., at a pressure of 70–100 psia, and standard space velocity of 1000–2000 v/v/hr. By carrying out the above process in the stated variable ranges efficient activity maintenance and production of $C_2$–$C_4$ olefins can be achieved.

The effluent gases in the process exiting from the reactor may be recycled if desired to the reactor for further CO hydrocarbon synthesis.

Methods for collecting the products in the process are known in the art and include distillation fractional distillation, and the like. Methods for analyzing the product liquid hydrocarbons and gaseous streams are also known in the art and generally include gas chromatography, liquid chromatography, high pressure liquid chromatography and the like.

Apparatus useful in the preferred process is any conventional slurry type reactor, being horizontal or vertical, being stationary or cyclical in catalyst slurry. Other apparatus not specifically described herein will be obvious to one skilled in the art from a reading of this disclosure.

The following examples set forth the best mode of carrying out the claimed invention as contemplated by the inventors and should not be construed as being limitations on the scope and spirit of the instant invention.

EXAMPLE 1

Experimental: A 300 cc Parr CSTR (continuous stirred tank reactor) was charged with 50 g of hexadecane, the indicated amount of iron and cobalt carbonyl precursors: $[CpFe(CO)_2]_2$ (I) and $Co_2(CO)_8$ (II) and the indicated amount of metal oxide support as listed in Table II. The reactor was sealed, purged with CO at room temperature and then heated to 200° C. over a 3-4 hour period with stirring under 100 psig of CO pressure. The system was then purged with $H_2$ while the temperature was increased to 220° C., where the system was maintained with stirring for a one-hr period. The system was then placed under CO/hydrogenation reaction conditions at 270° C., as indicated in Table I, and the gaseous effluent from the reactor was monitored by an HP-5840A Refinery Gas Analyzer to determine CO conversion and the nature of the formed hydrocarbon products.

TABLE I

Catalysts Charged to 300 cc Parr Reactor

| Run | $[CpFe(CO)_2]_2$, gms | $Co_2(CO)_8$, gms | Support (gms) |
|---|---|---|---|
| A | — | — | $Fe_2O_3$ (5) |
| B | — | — | $Fe_{2.85}Co_{.15}O_4/1\%$ K (5) |
| C | 1.52 | .47 | — |
| D | 1.52 | .47 | $Fe_2O_3/1\%$ K (5) |
| E | 1.52 | .47 | $Al_2O_3$ (10) |
| F | 1.52 | .47 | MgO (10) |
| G | 1.52 | .47 | MgO/1% Cu (5) |

TABLE II

Fe—Co Catalysts with 1:1 $H_2$:CO

| Run | Complex | Support | % CO Conv. | % $CO_2$ | % $CH_4$ | Selectivity % $C_2^=$-$C_4^=$ | % $C_2^o$-$C_4^o$ | % $C_5^+$ | $Cn^=/Cn^o_{(C_2-C_4)}$ |
|---|---|---|---|---|---|---|---|---|---|
| (A) | — | $Fe_2O_3$ | 5 | — | — | — | — | — | — |
| (B) | — | $Fe_{2.85}Co_{.15}O_4/1\%$ K | 5 | — | — | — | — | — | — |
| (C) | I + II | — | 25 | 35.4 | 15.4 | 17.8 | 5.3 | 26.1 | 3.4 |
| (D) | I + II | $Fe_2O_3/1\%$ K | 54 | 50 | 3.0 | 7.2 | 1.1 | 38.7 | 6.5 |
| (E) | I + II | $Al_2O_3$ | 21 | 25.0 | 20.0 | 18.3 | 9.0 | 27.7 | 2.0 |
| (F) | I + II | MgO | 30 | 35.0 | 18.6 | 16.1 | 6.8 | 23.5 | 2.4 |
| (G) | I + II | MgO/1% Cu | 26 | 50.0 | 9.6 | 14.7 | 3.8 | 21.9 | 3.9 |

Conditions:
270° C., 1:1 $H_2$:CO, 1200 V/V/hr, 70 psig, $C_{16}^+$ paraffin solvent, 600 rpm, Complex I $[CpFe(CO)_2]_2$ and Complex II $Co_2(CO)_8$.

As is seen from the data, the Fe-Co catalysts obtained from carbonyl precursors are more active for $C_2$-$C_4$ olefin production than the related ex situ prepared catalysts in runs A and B.

EXAMPLE 2

Using the apparatus and general procedure of Example 1, the following CO/hydrogenation runs were made @250° C. The results are listed below in Table III.

TABLE III

Fe—Co Catalysts with 1:1 $H_2$:CO

| Run | Complex | Support | % CO Conv. | % $CO_2$ | % $CH_4$ | Selectivity % $C_2^=$-$C_4^=$ | % $C_2^o$-$C_4^o$ | % $C_5^+$ | $Cn^=/Cn^o_{(C_2-C_4)}$ |
|---|---|---|---|---|---|---|---|---|---|
| (A) | — | $Fe_2O_3$ | <5 | >20 | tr | tr | tr | tr | tr |
| (B) | — | $Fe_{2.85}Co_{.15}O_4/1\%$ K | <5* | — | — | — | — | — | — |
| (C) | I + II | — | 20 | 14.3 | 6.4 | 11.8 | 1.7 | 65.8 | 6.9 |
| (D) | I + II | $Fe_2O_3/1\%$ K | 39 | 38.5 | 7.4 | 5.6 | 1.8 | 46.7 | 3.1 |
| (E) | I + II | $Al_2O_3$ | 44 | 10.3 | 14.6 | 8.3 | 7.7 | 59.1 | 1.1 |
| (F) | I + II | MgO | 28 | 17.9 | 13.4 | 5.5 | 5.1 | 58.1 | 1.1 |
| (G) | I + II | MgO/1% Cu | 42 | 31.5 | 8.7 | 8.9 | 2.8 | 48.1 | 3.2 |

Conditions:
250° C., 1:1 $H_2$:CO, V/V/hr, 70 psig, $C_{16}^+$ paraffin solvent, 600 rpm, *<5% CO conversion observed even at 270° C.

As is seen from the data in Tables II and III, comparative results for conventional iron and iron-cobalt catalysts, Runs A and B in Tables II and III, indicate that these systems provide marginal catalytic activity under the mild reaction conditions employed in this study. In contrast, catalysts derived from $[CpFe(CO)_2]_2$ and $Co_2(CO)_8$ show increased activity and reasonably good selectivity for production of $C_2^+$ olefins, see Runs C-G in Tables II and III. In two cases, Runs D and G, this system is ca 5 to 10-fold more active than the conventional catalysts and has $CH_4$ selectivity of <10% which is superior to that found with any of the published Fe-Co catalysts, i.e. where $CH_4$ selectivity is typically >20%. The relatively mild conditions and low pressures employed with the catalyst of this invention are favorable for alpha-olefin production and subsequent processing steps to remove these products from the reaction zone.

EXAMPLE 3

Using the apparatus and general CO/hydrogenation procedure described in Example 1, the following runs were carried out under the specific conditions listed in Table IV below, with Catalyst F, and the listed results.

TABLE IV

Performance of $[CpFe(CO)_2]_2/Co_2(CO)_8/MgO$

| Pressure psig | 50 | 70 |
|---|---|---|
| % CO Conversion (total) | 27.0 | 33.0 |
| (To $CO_2$) | 9.2 | 9.9 |
| Wt. % Selectivity | | |
| $CH_4$ | 23.7 | 21.7 |
| $C_2^=$ | 3.5 | 2.4 |
| $C_2^o$ | 3.6 | 3.7 |
| $C_3^=$ | 12.6 | 11.1 |
| $C_3^o$ | 1.8 | 2.3 |

TABLE IV-continued

| Performance of [Cp Fe(CO)$_2$]$_2$/Co$_2$(CO)$_8$/MgO | | |
| --- | --- | --- |
| C$_4$= | 5.5 | 5.3 |
| C$_4$° | 1.5 | 2.0 |
| C$_5$+ | 47.8 | 51.5 |
| % Olefin in C$_{2-4}$ | 76 | 70.0 |

Conditions: 270° C., 1:1 H2:CO, 1000 V/V CAT/hr SHSV, 600 rpm, octacosane solvent, 96 hr. on stream time.

As is seen from the data, a modest increase in reaction pressure, while all other conditions are maintained at a constant level, leads to a slight reduction in CH$_4$ selectivity, a decrease in the olefin content of the C$_{2-4}$ fraction and a modest increase in activity. Increased pressure also leads to a modest increase in selectivity to C$_5$+ products 47.8 to 51.5% for 50 to 70 psig respectively.

EXAMPLE 4

Using the apparatus and general CO/hydrogenation procedure described in Example 1, the following runs were conducted @ the specific conditions listed in Table V below with Catalyst E, containing the listed results.

TABLE V

| Performance of [Cp Fe(CO)$_2$]$_2$/Co$_2$(CO)$_8$/Al$_2$O$_3$ | | |
| --- | --- | --- |
| Pressure psig | 70 | 100 |
| % CO Conversion | 27.0 | 33.0 |
| To CO$_2$ | 9.2 | 9.9 |
| Wt. % Selectivity | | |
| CH$_4$ | 19.8 | 18.2 |
| C$_2$= | tr | 1.8 |
| C$_2$° | 2.6 | 3.3 |
| C$_3$= | 9.0 | 10.8 |
| C$_3$° | 2.5 | 2.4 |
| C$_4$= | 3.9 | 4.3 |
| C$_4$° | 1.7 | 2.0 |
| C$_5$+ | 60.5 | 57.2 |
| % Olefin in C$_{2-4}$ | 68.0 | 68.7 |

Conditions: 270° C., 1:1 H2:CO, 1000-1200 V/V CAT/hr, 600 rpm, octacosane solvent, 96 hr. on stream time.

As is seen, analysis of the Al$_2$O$_3$ supported catalyst at 70 and 100 psig reveals that as the catalyst activity increases, as measured by %CO conversion, CH$_4$ selectivity decreases and the olefin content of the C$_{2-4}$ fraction remains nearly constant as the pressure increases. A slight drop in the C$_5$+ selectivity was noted as pressure was raised from 70 to 100 psig. Advantageously the CH$_4$ selectivity with the present catalyst remained at a fairly low level, despite the pressure increase from 70 to 100 psig.

What is claimed is:

1. A process for preparing a slurry Fischer-Tropsch catalyst system comprising the steps of:
    (a) heating a slurry mixture comprised of: a Fischer-Tropsch slurry liquid, an iron carbonyl compound, a cobalt carbonyl compound, or iron and cobalt compounds capable of forming carbonyl complexes in an atmosphere of CO, and mixtures thereof, and a powdered support, wherein said iron and cobalt compounds are present in a total iron:cobalt atomic ratio of about 35:1 to 1:10, taken as free metals, and wherein the cobalt carbonyl compound has a lower melting point/decomposition temperature than the iron carbonyl compound; in a carbon monoxide atmosphere under pressure, at a temperature above the melting point/decomposition temperature of the cobalt compound for a time sufficient to substantially decompose the cobalt compound; and
    (b) heating said slurry mixture from step (a) at a temperature above the melting point/decomposition temperature of the iron compound in said CO atmosphere under pressure, to substantially decompose the iron compound; and
    (c) heating said slurry mixture from step (b) in an atmosphere of hydrogen gas to substantially reduce said iron and cobalt carbonyl compounds and their decomposition products.

2. The process of claim 1 wherein said iron compound is selected from Fe$_3$CO$_{12}$, [CpFe(CO)$_2$]$_2$, and (Cp)$_2$Fe, wherein Cp is the cyclopentadienyl ligand, C$_5$H$_5$.

3. The process of claim 1 wherein said cobalt carbonyl is selected from CO$_2$(CO)$_8$, CpCo(CO)$_2$ and, Cp$_2$Co wherein Cp is the cyclopentadienyl ligand, C$_5$H$_5$.

4. The process of claim 1 wherein said support is selected from iron oxide, alumina, magnesia, CeO$_2$, SiO$_2$, mixtures thereof, and the like.

5. The process of claim 1 wherein said support is present in a 10 to 99 weight percent based on the total combined weight of said iron and cobalt carbonyl compounds and support.

6. The process of claim 1 wherein said slurry in step (a) further comprises a promoter agent.

7. The process of claim 6 wherein said promoter agent is potassium carbonate.

8. The process of claim 1 wherein said slurry liquid is selected from high boiling point aliphatic and aromatic hydrocarbons, ethers and amines.

9. The process of claim 8 wherein said slurry liquid is selected from octacosane, hexadecane, or mixtures thereof.

10. The process of claim 1 wherein said slurry liquid is present in about a 50:1 to 99:1 weight ratio to the total weight of iron and cobalt carbonyl compounds plus support and promoter agent.

11. The process of claim 1 wherein said temperature in step (a) is 60° to 250° C.

12. The process of claim 1 wherein said temperature in step (b) is 100° to 300° C.

13. The process of claim 1 wherein said temperature in step (c) is 100° to 300° C.

14. The process of claim 1 wherein said CO partial pressure in step (a) is 15 to 200 psia.

15. The process of claim 1 wherein said CO partial pressure in step (b) is 15 to 200 psia.

16. The process of claim 1 wherein said hydrogen partial pressure in step (c) is 15 to 200 psia.

17. The process of claim 1 wherein said iron compound is of the formula [CpFe(CO)$_2$]$_2$, said cobalt compound is of the formula Co$_2$(CO)$_8$ and said support is Fe$_2$O$_3$, the support having 1 weight percent potassium carbonate deposited thereon and wherein Cp is the cyclopentadienyl ligand, C$_5$H$_5$.

18. A process for preparing a Fischer-Tropsch slurry catalyst system comprising the steps of:
    (a) heating a slurry mixture comprising octacosane; (CO$_2$(CO)$_8$), [CpFe(CO$_2$)]$_2$, plus Fe$_2$O$_3$/1%K, in a respective weight ratio of 0.094:0.304:1.0 at a temperature of about 200° C., and under a carbon monoxide partial pressure of about 100 psig for a time sufficient to substantially decompose said cobalt and iron carbonyl compound, wherein Cp is the cyclopentadienyl ligand, C$_5$H$_5$; and
    (b) heating said reaction mixture from step (a) in an atmosphere of hydrogen gas at a temperature of 220° C. and 100 psig pressure of hydrogen, for a time sufficient to substantially reduce the starting iron and cobalt compounds and their decomposition products.

* * * * *